(12) United States Patent
Overweg

(10) Patent No.: US 10,173,077 B2
(45) Date of Patent: Jan. 8, 2019

(54) THERAPEUTIC APPARATUS

(75) Inventor: Johannes Adrianus Overweg, Uelzen (DE)

(73) Assignee: KONINKLIJKE PHILIPS ELECTRONICS N.V., Eindhoven (NL)

(*) Notice: Subject to any disclaimer, the term of this patent is extended or adjusted under 35 U.S.C. 154(b) by 847 days.

(21) Appl. No.: 13/131,476

(22) PCT Filed: Nov. 19, 2009

(86) PCT No.: PCT/IB2009/055169
§ 371 (c)(1),
(2), (4) Date: May 26, 2011

(87) PCT Pub. No.: WO2010/067227
PCT Pub. Date: Jun. 17, 2010

(65) Prior Publication Data
US 2011/0230754 A1    Sep. 22, 2011

(30) Foreign Application Priority Data
Dec. 12, 2008  (EP) .................................. 08171553

(51) Int. Cl.
*A61N 5/10*    (2006.01)
*A61N 5/00*    (2006.01)

(52) U.S. Cl.
CPC .......... *A61N 5/1049* (2013.01); *A61N 5/1037* (2013.01); *A61N 5/1038* (2013.01);
(Continued)

(58) Field of Classification Search
CPC .... A61N 2005/1055; A61N 2005/1087; A61B 5/055
(Continued)

(56) References Cited

U.S. PATENT DOCUMENTS 6,198,957 B1 * 3/2001 Green ........................... 600/411
6,725,078 B2   4/2004 Bucholz et al.
(Continued)

FOREIGN PATENT DOCUMENTS

EP    1121957 A2    8/2001
EP    1525901 A1    4/2005
(Continued)

OTHER PUBLICATIONS

Raaymakers et al: "Feasibility of MRI Guided Proton Therapy: Magnetic Field Dose Effects"; Med. Biol. 53, (2008), pp. 5615-5622.
(Continued)

*Primary Examiner* — Patricia Park

(57) ABSTRACT

A therapeutic apparatus comprising: a magnetic resonance imaging system adapted for acquiring a set of magnetic resonance imaging data in an imaging zone, wherein the magnetic resonance imaging system comprises a means for generating a magnetic field, a guiding means adapted for guiding a beam of charged particles to a target zone within a subject such that the beam encloses an angle with the magnetic field lines of the magnetic field within the imaging zone, the angle being between 0 degrees and 30 degrees, wherein the imaging zone comprises the target zone, a zone determination means for determining the location of the target zone within the subject using the set of magnetic resonance imaging data.

7 Claims, 4 Drawing Sheets

(52) U.S. Cl.
CPC ............... *A61N 2005/1055* (2013.01); *A61N 2005/1087* (2013.01)

(58) Field of Classification Search
USPC ........................................................ 600/411
See application file for complete search history.

(56) References Cited

U.S. PATENT DOCUMENTS

| | | | | |
|---|---|---|---|---|
| 6,730,921 | B2* | 5/2004 | Kraft | 250/492.1 |
| 2004/0199068 | A1* | 10/2004 | Bucholz et al. | 600/411 |
| 2005/0197564 | A1* | 9/2005 | Dempsey | A61B 5/055 600/411 |
| 2006/0245543 | A1* | 11/2006 | Earnst et al. | 378/65 |
| 2006/0267585 | A1 | 11/2006 | Havens | |
| 2007/0041500 | A1 | 2/2007 | Olivera et al. | |
| 2007/0225603 | A1* | 9/2007 | Jackson | 600/436 |
| 2009/0041200 | A1* | 2/2009 | Lu | A61N 5/1042 378/152 |
| 2009/0088625 | A1* | 4/2009 | Oosting et al. | 600/411 |
| 2009/0234219 | A1 | 9/2009 | Kruip | |
| 2009/0296885 | A1* | 12/2009 | Boeh et al. | 378/65 |
| 2010/0013418 | A1 | 1/2010 | Kruip et al. | |

FOREIGN PATENT DOCUMENTS

| | | |
|---|---|---|
| EP | 1974770 A1 | 10/2008 |
| JP | 2003126278 A | 5/2003 |
| JP | 2008022896 A | 2/2008 |
| WO | 9932189 A1 | 7/1999 |
| WO | 2007017847 A1 | 2/2007 |
| WO | 2007045076 A1 | 4/2007 |

OTHER PUBLICATIONS

Liu, Hong-Yong "Study of Motion Track for an Electric Particle in Uniform Electristatic or Magnetic Fields" Journal of Sichuan Normal Univeristy (Natural Science), Jul. 1999, vol. 22. No. 4.

Greco et al "Current Status of Radiotherapy With Proton and Light Ion Beams" Cancer, vol. 109, no. 7 (Apr. 1, 2007) p_ 1227-1238.

Schulte, R. "Applications of Silicon Detectors in Proton Radiobiology and Radiation Therapy" Powerpoint presentation, 'Sep. 16, 2014) Loma Linda University Medical Center.

* cited by examiner

THERAPEUTIC APPARATUS

FIELD OF THE INVENTION

The invention relates to the guiding of charged particles to a target zone within a subject.

BACKGROUND OF THE INVENTION

In charged particle beam therapy, an energetic charged particle beam is directed at a target zone of a subject. The primary mechanism for the interaction of such a beam comprising charged particles with matter is through the Coulomb force. The cross section for Coulomb collisions increases as the relative velocity of two particles decreases. As a charged particle beam travels through a subject, it loses energy more and more rapidly. The effect of this is that the majority of the energy of the particle beam is deposited near the end of the beam path. There is therefore a large peak of energy deposited at the end of the beam path which is called the Bragg peak.

For this reason, charged particle beam therapy allows very precise delivery of high dose to a tumor target while minimizing the total dose to the subject. However, even small movements of anatomical structures in the path of the beam can lead to significant deviations of the delivered dose from the original dose plan. Therefore, it is desirable to use real-time imaging to track the target and adapt the beam to the motion of organs and of the target.

For charged particle beam therapy, real-time MRI during the delivery of the beam has been unfeasible, because the strong magnetic fields associated with MRI will dramatically impact the path of the charged particles towards the target.

A static magnetic field is used by Magnetic Resonance Imaging (MRI) scanners to align the nuclear spins of atoms as part of the procedure for producing images within the body of a subject. During an MRI scan, Radio Frequency (RF) pulses generated by a transmitter coil cause perturbations to the local magnetic field, and RF signals emitted by the nuclear spins are detected by a receiver coil. These RF signals are used to construct the MRI images. These coils can also be referred to as antennas. Further, the transmitter and receiver coils can also be integrated into a single transceiver coil that performs both functions. It is understood that the use of the term transceiver coil also refers to systems where separate transmitter and receiver coils are used.

U.S. Pat. No. 6,675,078 and corresponding European patent EP 1 121 957 A2 describes a therapeutic apparatus which combines proton beam therapy with MRI. MRI is used for targeting and gating the proton beam therapy.

PCT patent application WO 99/32189 relates to a combined MRI and radiotherapy system. The system described has a magnetic resonance imaging system, a gantry mounted set of coils for generating a magnetic field that rotates with a guiding system for a radiotherapy beam, and it uses MRI to detect the effect of the radiotherapy on an irradiated region.

SUMMARY OF THE INVENTION

The invention provides for a therapeutic apparatus as claimed in claim 1. Embodiments of the invention are given in the dependent claims.

In accordance with an embodiment of the invention, the therapeutic apparatus comprises a vertical field MRI scanner in combination with a fixed charged particle guiding means, entering through an opening at the top of the magnet. Vertical field MRI scanners are also known as high-field-open MRI scanners. This arrangement reduces the curvature of charged particle paths due to the magnetic field of the MRI magnet. In one embodiment, the charged particle beam is oriented at an angle of approximately 20 degrees relative to the vertical axis of the magnet. This allows the application of multiple field treatment by rotating the subject support about the vertical axis, without the need for a complicated rotation system on the charged particle beam line.

Embodiments of the invention provide for a therapeutic apparatus comprising a magnetic resonance imaging system adapted for acquiring a set of magnetic resonance imaging data in an imaging zone, wherein the magnetic resonance imaging system comprises a means for generating a magnetic field. The therapeutic apparatus further comprises a guiding means adapted for guiding a beam of charged particles to a target zone within a subject such as the beam encloses an angle of magnetic field lines of the magnetic field within an imaging zone, the angle being between 0 degrees and 30 degrees, wherein the imaging zone comprises the target zone. The therapeutic apparatus further comprises a zone determination means for determining the location of the target zone within the subject using a set of magnetic resonance imaging data.

By restricting the angle which the particle beam makes with respect to the magnetic field lines in an imaging zone, the effect of the magnetic field on the trajectory of the beam of charged particles is reduced. This is because the velocity component parallel to the magnetic field lines is not affected by the magnetic field. The velocity component perpendicular to the magnetic field lines causes a precession around the magnetic field lines and causes a spiral-like orbit around the field lines.

The direction and magnitude of the magnetic field in the imaging zone and in the other parts of the magnet through which the beam passes is known with high precision and the trajectory of the charged particles can be predicted with high precision.

The guiding means can guide a beam of charged particles from a particle accelerator. Examples of charged particle accelerators that can be used are a cyclotron, a synchrotron, or a linear accelerator. The guiding means can comprise a system to guide the energetic particles to the magnetic resonance imaging system; the guiding means can also comprise charged particle optics for changing the trajectory of the charged particles that comprise the beam of charged particles. The zone determination means can be implemented as a computer program product that is able to segment the magnetic resonance imaging data and determine the location of the target zone and also of structures within the subject that surround the target zone and lie in the beam path. The guiding means can contain charged particle mirrors and also charged plates and objects for deflecting the trajectory of the charged particle beam.

The pulse sequences used for acquiring magnetic resonance imaging data can be tailored to locate the target zone, and also to locate high risk organs that can be easily damaged by a charged particle beam.

In another embodiment, the charged particles comprising the beam have a kinetic energy greater than or equal to the kinetic energy necessary so that the Bragg peak of the particle beam is within the target zone. The Bragg peak is the location where the majority of the energy from the charged particle beam is deposited. This embodiment is advantageous, because the charged particles have enough energy to reach the target zone.

In another embodiment, the beam control means further comprises an adjustable attenuator for modulating the location of the Bragg peak of the beam so that the Bragg peak is within the target zone. This embodiment is advantageous, because an attenuator is able to change the energy of the particles comprising the charged particle beam. This effects how far the particles can penetrate into the subject and determines where the majority of energy is deposited. Using an attenuator is advantageous, because the energy of the charged particle beam can be adjusted very rapidly and can be used to compensate for external and internal motion of the subject. Depositing the majority of the energy in the target zone is critical, because the deposition of energy by a particle beam is localized and if the beam is directed to an area outside of the target zone, the subject can be damaged.

In another embodiment, the therapeutic apparatus further comprises a trajectory calculation means for calculating the trajectory of a beam using magnetic field data being descriptive of the magnetic field such that the calculated trajectories reaches the target zone, and a control means adapted for controlling the guiding means using the calculated trajectory such that the beam follows the calculated trajectory.

The magnetic resonance imaging system comprises a means for generating a magnetic field. This can be a superconducting magnet. An effect of the large magnetic field used for magnetic resonance imaging is that the magnetic field deflects the trajectory of charged particles in a magnetic field. However, using the magnetic field data, the trajectory of the charged particle beam in the magnetic field can be calculated exactly. This allows the guiding means to guide the beam of charged particles to the target zone within the subject.

This embodiment is advantageous, because knowledge of the magnetic field data can be used to calculate the trajectory of the charged particles. In this way, charged particle beams can be directed exactly to the target zone. This reduces the probability that the particle beam will be directed towards a region outside of the target zone and damage the subject.

The magnetic field data can be magnetic field data that is calculated from a knowledge of the design of the means for generating a magnetic field, or it can be measured directly and stored for later recall, for example in a lookup table. This can be implemented by using magnetic field data and then calculating the trajectory of the charged particles in the beam with small time steps. Essentially, the equation of motion of the particle is integrated in time.

The control means can be implemented as a computer or as a controller and can be adapted for controlling the guiding means such that the trajectory of the beam follows the trajectory that was calculated by the calculation means.

In another embodiment, the trajectory calculation means is adapted for calculating an energy loss of the charged particles comprising the beam within the subject, and the trajectory calculation means adjusts the calculated trajectory using the energy loss. This is advantageous, because as a charged particle beam passes through matter it gradually loses energy. The energy change will affect the trajectory of charged particles within the magnetic field. The slower the velocity of a particle, the more curvature there will be in a constant magnetic field, and taking this into account allows the trajectory to be calculated accurately.

In another embodiment, the guiding means is further adapted such that the beam encloses an angle between 5 degrees and 25 degrees with magnetic field lines of the magnetic field within the imaging zone, the angle being preferably between 15 and 20 degrees. The trajectory calculation means is adapted for calculating more than one calculated trajectory of the beam that directs the beam to the target zone, wherein the beam control means is adapted for switching between the more than one calculated beam trajectory to minimize the exposure of portions of the subject outside of the target zone to the beam.

This embodiment can be advantageous, because when the particle beam makes a slight angle with the field lines, the trajectory spirals around the field lines in a circular manner. This means that if the trajectory and energy of the beam is changed that more than one trajectory to the target zone can be found. This is advantageous, because more than one path can be found through the subject to the target zone with the particle beam. This can be used to reduce the radiation dose received by regions outside of the target zone. The radiation dose can be spread over a larger portion of the subject and thereby reduces the chance for unintended damage.

In another embodiment, the MRI system is adapted for acquiring the set of magnetic resonance imaging data at periodic intervals. This is advantageous because MRI data can be acquired repeatedly and used to track the motion of the target zone, motion of the subject, and also of internal motion within the subject. In this embodiment the zone determination means is further adapted to monitor motion of the target zone using a set of magnetic resonance imaging data acquired at periodic intervals. This can be implemented by segmentation algorithms which are able to detect the location of the zone determination means and also of surrounding organs which can be damaged by the charged particle beam.

The zone determination means is further adapted to monitor internal motion of the subject along the beam trajectory using the set of magnetic resonance imaging data acquired at periodic intervals. This includes internal motion both perpendicular and parallel to the beam trajectory. This is advantageous, because there can be internal motion within a subject which can affect the trajectory of the particle beam, for instance if the particle beam is traveling through soft tissue or through bony material such as a rib, the attenuation of the particle beam will be different. The trajectory calculation means can then use this information to properly calculate a trajectory which directs the particle beam to the target zone. For this reason the trajectory calculation means is adapted to compensate for motion of the target zone and of the subject along the beam trajectory used during calculation of the trajectory. The interval at which MRI data is acquired is determined by the rate of the movement which should be compensated for. For instance to compensate for the filling of a bladder, MRI data is acquired at a slower rate than if breathing is compensated for.

In another embodiment, the guiding means comprises charged particle optics for adjusting the beam trajectory, and an adjustable attenuator for modulating the energy of charged particles comprising the beam. The charged particle optics can be comprised of magnets, electromagnets and also electrodes and structures which can be built up to large voltage potentials. These produce magnetic or electric fields which can be used to deflect or adjust the trajectory of the charged particle beam.

The adjustable attenuator can be implemented as an object which interrupts the path of the charged particles comprising the beam. The charged particles interact predominantly with the matter they travel through using the Coulomb force. As a result, as the velocity of the charged particles becomes slower, their interaction with the surrounding matter becomes more likely. The effect of the attenuator is to reduce the energy of the charged particles comprising the beam. The effect of this is that it reduces the depth to which the charged particle beam can penetrate into the subject. The attenuator can be placed anywhere between the source of the charged particle beam to just before the beam enters the subject. If the attenuator is before or within the guiding means, then the energy of the charged particle beam will change, and this change in energy will need to be accounted for and the guiding means will need to be able to adapt to the change in energy to ensure that the beam of charged particles has the correct trajectory through it.

Placing the attenuator closer to the subject has the advantage that many portions of the guiding means will not need to be adaptable to the changing energy of the particle beam. A disadvantage is that there is a probability that charged particles such as protons can cause a nuclear reaction which would cause the attenuator to become radioactive. However, this depends upon the type of charged particle being used and also the material which is used as an attenuator.

In another embodiment, the guiding means is adapted for being moved relative to the means for generating a magnetic field. This embodiment is advantageous, because the guiding means can be moved to different locations and in this way a variety of trajectories to the same target zone can be found. This allows the radiation dose to be received by the subject not in the target zone over a larger area. This reduces the chance of damage to the subject.

In another embodiment, the therapeutic apparatus further comprises a subject support adapted for adjusting the position of the subject during operation of the therapeutic apparatus. This embodiment is advantageous, because subject support can change the position of the subject relative to the particle beam during therapy.

In another embodiment, the orientation of the guiding means is fixed relative to the means for generating a magnetic field and wherein the subject support is further adapted for rotational motion during operation of the therapeutic apparatus.

This embodiment is advantageous, because the rotational motion of the subject support is able to move the subject into various positions within the beam. This allows all regions of the subject to be reached with the beam and it also allows multiple paths for a beam through the subject to reach the target zone.

In another embodiment, the zone determination means is further adapted for receiving planning data for planning therapy. The zone determination means is also adapted for confirming if the planning data satisfies a predetermined criterion using a set of magnetic resonance imaging data. When therapy is performed with a charged particle beam, a physician will normally take three-dimensional images of the subject using a medical imaging system such as magnetic resonance imaging or computer tomography with X-ray and then plan the treatment of the subject based on this three-dimensional data. This embodiment has the advantage that the zone determination means confirms if the planning data satisfies a predetermined criterion and determines if the anatomy of the subject is indeed close to the anatomy that was used when the planning data was generated.

Due to the large cost of particle accelerators it is possible that the planning data can be generated at a site using a different medical imaging system which is part of the therapeutic apparatus. Also the internal anatomy of the subject could have changed since the planning was performed by the physician. For example the person could have more fat, or in the case of treating a prostate the latter could be filled with more liquid or less liquid than it was during the planning. The planning data can be verified by comparison with a predetermined criterion. If the planning data does not satisfy a predetermined criterion, at least one of the following actions can be performed: halting the generation of the beam of charged particles, alerting an operator that the planning data is not accurate, adjusting the planning data, or receiving corrections to the planning data from the operator. If the planning data is not accurate then it is beneficial to halt the generation of the beam of charged particles, because this prevents the charged particles from traversing a region of the subject that was not intended. Alerting an operator that the planning data is not accurate is advantageous, because the operator then knows that there is sufficient discrepancy between the anatomy of the subject and the anatomy used during planning that the treatment will not proceed properly. The zone determination means can be implemented using segmentation algorithms and the planning data can be adjusted using the segmented MRI images. This is advantageous, because small changes in the anatomy can be compensated for automatically by the system. In addition, movement and breathing can be compensated for in the treatment plan. For instance, the movement of ribs in and out of the beam path due breathing can cause errors during therapy. However using the MRI images this movement can be accounted for and the treatment plan can be adjusted.

Receiving corrections to the planning data is advantageous, because a skilled operator or physician can then manually make corrections to the planning data.

In another embodiment, the magnetic resonance imaging system is adapted for measuring the trajectory of the charged particles within the image zone. The beam control means is adapted for adjusting the beam trajectory using the measured trajectory. This embodiment it is particularly advantageous, because the magnetic resonance imaging system is able to directly measure the path that the charged particle beam takes. This information is then used by the beam control means to adjust the beam trajectory. This provides verification of the calculated trajectory, and also reduces the chance that areas outside of the target zone of the subject will not be irradiated by the particle beam. The trajectory of the particle beam can be measured by magnetic resonance imaging using several different methods:

Method 1: Use the therapy charged particle beam as means of MR excitation, by pulsing the beam at the MR Larmor frequency or at a sub-harmonic of the Larmor frequency.

Method 2: Use the de-phasing effect of the Root Mean Square (RMS) beam current in combination with a BOLD-like MR sequence.

Method 3: Use the de-phasing effect due to paramagnetic behavior of beam interaction products An estimate showing the viability of detecting a proton beam is made using the following assumptions:

The proton beam is very narrow, with lateral dimensions up to the Bragg zone of less than 1 mm, preferably less than 0.1 mm.

The beam consists of short pulses with a repetition frequency in the range 50-100 MHz and a peak beam current of the order of 100 microampere The RMS beam current can reach a level of 0.1 microampere (current levels in clinical therapy systems are 0.01-0.02 microampere)

The duration of the train of proton pulses required for one treatment session is of the order of minutes Using these assumptions, the beam current generates a magnetic field circulating around its trajectory. The field drops off with 1/r (r being the distance to the center of the beam). At a radius of 0.1 mm, the B field due to a current of 0.1 microampere is 1.3 nanotesla. For 100 microampere the field at 0.1 mm is 1.3 microtesla.

Example of Method 1

The pulses coming from the proton accelerator have a high and very stable repetition frequency of the order of 100 MHz (this is a design parameter of the cyclotron or synchrotron generating the protons). The MRI system and the proton accelerator can be matched to each other in such a way that the beam pulse repetition frequency is exactly equal to the MR resonance frequency. Then the field around the proton beam acts on the tissue protons as a steady MR excitation pulse. The MR effect of the beam RF field can be switched on and off by either slightly modifying the pulse repetition frequency of the accelerator or by adding a small offset-field to the field of the MR background magnet (using a B0 coil incorporated in the gradient coil system). The MR excitation effect of the beam field can be converted into a visible effect in images in many ways. One way would be to use the beam field as the only MR excitation and to make an image using the resulting MR signal. Such imaging can be performed very rapidly because only voxels very close to the beam will emit signal. In principle, the beam can be reconstructed from three projections. Alternatively, the effect of the beam-related RF field can be used as an RF pre-pulse (such as in an inversion recovery sequence), modulating the signal coming from the voxels through which the beam passes. It is also conceivable to use the beam RF field as a saturation pulse, suppressing the generation of RF signals from the voxels through which the beam passes. The MR excitation effect will also occur if the repetition frequency of the proton pulses is a phase-synchronous sub-harmonic of the Larmor frequency. In general, if the frequency spectrum of the train of proton pulses contains a frequency component at the Larmor frequency, this train of proton pulses will cause MR excitation.

A therapeutic apparatus adapted to image the beam may have one or more of the following design features:

Identical frequencies for MR resonance and proton beam pulse repetition

Accurate frequency lock between the sub-systems

A means to switch between MR resonance and off-resonance by either modulating the accelerator frequency or the total B0 field of the MR scanner Example of Method 2

The RMS beam current generates an RMS magnetic field around the beam which modulates the resonance frequency in the voxels through which the beam passes. At an average beam current of 0.1 microamperes, the frequency offset at 0.1 mm from the center of the beam is about 0.05 Hz. Using a MR detection method such as Blood Oxygen Level Dependent (BOLD) contrast functional imaging, this frequency offset can be visualized. Visualizing the beam using this method will involve periodically interrupting the transmission of the proton beam and to compare MR images with and without the proton beam being transmitted. In order to enhance the visibility of the proton beam the RMS beam current can be increased during the time when the MR de-phasing effect is required. For example, the average current can be kept at a level of 0.02 microampere for most of the time (the current practical clinical level) but increased to 0.2-1.0 microampere in intervals between the RF excitation pulse and the start of the MR acquisition window. In this case, the duty cycle of the enhanced amplitude part of the beam current could be of the order of 5%. Such a limited high-amplitude operation of the proton delivery system is probably acceptable if the current is being limited by heating of components.

Example of Method 3

The protons will result in ionization of the tissue. The free radicals thus formed will be paramagnetic and will result in a local decrease in the T2 relaxation time of the tissue. This effect can therefore be visualized using T2 sensitive imaging sequences.

In another embodiment, the charged particle beam comprises at least one of the following: protons, carbon nuclei, or atomic nuclei. The use of protons, carbon nuclei or another atomic nuclei is beneficial, because with their large mass they will be able to penetrate into a subject if the charged particle beam has sufficient energy.

In another embodiment, the means for generating a magnetic field comprise at least a first sub-magnet and a second sub-magnet, wherein the first and second sub-magnets are arranged so that the imaging zone is between the first and second sub-magnets, wherein the first sub-magnet surrounds a first central region, wherein the second sub-magnet surrounds a second central region, wherein the magnetic field lines of the means for generating magnetic field pass through the first central region and the central region. This embodiment is advantageous, because there can be a large region between the two sub-magnets adapted for receiving a subject.

In another embodiment, the first sub-magnet has an external surface facing away from the means for generating a magnetic field that intersects a first central service that surrounds the central region of the first magnet, wherein there is a beveled surface between the external surface and the first central surface which allows the beam to pass. This embodiment is advantageous, because it allows the particle beam to be launched at a larger angle with respect to the field lines in the imaging zone.

BRIEF DESCRIPTION OF THE DRAWINGS

In the following preferred embodiments of the invention will be described, by way of example only, and with reference to the drawings in which.

DETAILED DESCRIPTION

Like numbered elements in these figures are either identical elements or perform the same function. Numerals with the same last two digits also represent elements which are either identical or perform the same function. Elements which have been discussed previously will not necessarily be discussed in later figures if the function is identical.

Figure 1:
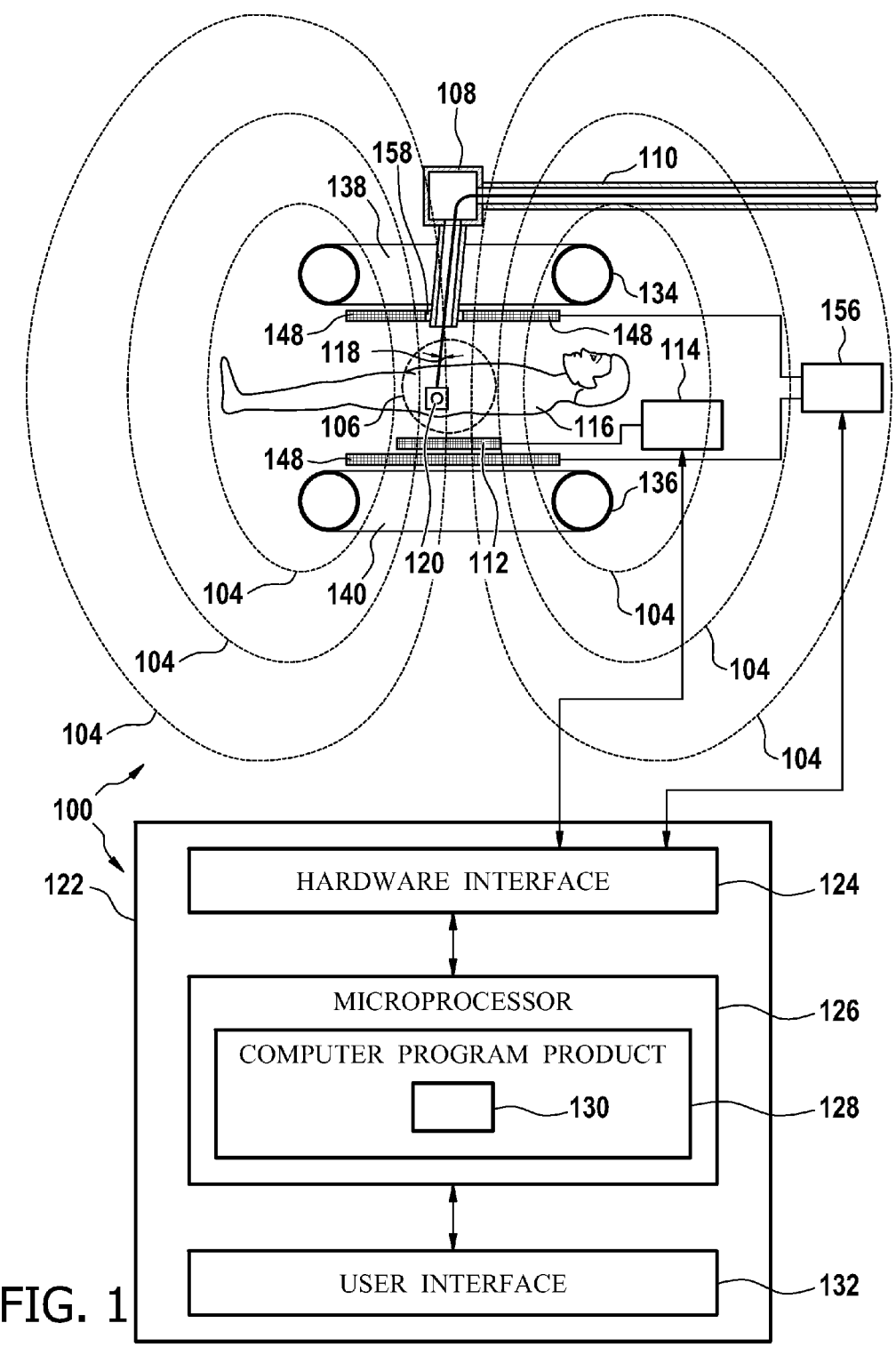
FIG. 1 shows an idealized, cross sectional view of an embodiment of a therapeutic apparatus according to an embodiment of the invention.

FIG. 1 shows an idealized cross-sectional view of an embodiment of a therapeutic apparatus according to an embodiment of the invention. This figure shows an MRI system 100 and a guiding means 108 adapted for guiding a beam of charged particles 110. The MRI system 100 comprises a first sub-magnet 134 and a second sub-magnet 136. These two sub-magnets 134, 136 are cylindrical and the magnetic field lines pass through the center of both sub-magnets 134, 136. There is an imaging zone 106 in which the magnetic field lines 104 are for all intents and purposes parallel with each other. Within this region it is possible to make MRI images of a subject 116. To acquire MRI images a transceiver coil 112 is used. The transceiver coil 112 is connected to an RF transceiver 114 and the transceiver 114 communicates with the hardware interface 124 of a computer 122. Spatial encoding of the MRI data is performed by means of gradient coils 148. In this embodiment, there is a gradient coil 148 adjacent to both of the sub-magnets 134, 136. The gradient coil 148 to the first sub-magnet 134 has an opening 158 adapted to receive a beam tube of the guiding means 108. This opening allows the charged particle beam 110 to pass through the gradient coil 148. In another embodiment, there is an RF coil 112 mounted next to both gradient coils 148. In this embodiment there can also be an opening in the RF coil 112. In other embodiments the RF coil 112 can rests upon the subject 116 or can be held by a holder adapted to receive an RF coil 112.

The computer 122 further comprises a microprocessor 126 and a user interface 132. The user interface 132 is adapted for receiving instructions and displaying data to an operator. The microprocessor 126 is adapted for executing a computer program product 128. The computer program product can be adapted for controlling and running the MRI system 100, the guiding means 108, and a particle accelerator. The computer program product comprises a zone determination means 130. The zone determination means 130 can be implemented as a segmentation module which is adapted for segmenting MRI data and determining a location of the target zone 120 and of internal organs and anatomy of a subject 116.

The guiding means 108 launches a beam of charged particles 110 at a target zone 120 within the imaging zone 106. Within the imaging zone 106, the trajectory of the particle beam 110 forms an angle 118. The angle 118 that the trajectory of the particle beam 110 makes relative to the field lines 104 and the strength of the magnetic field determine how much the particle beam is deflected by the magnetic field. It can be seen in this figure that the magnetic field lines 104 pass through the first central region 138 and the second central region 140.

Figure 2:
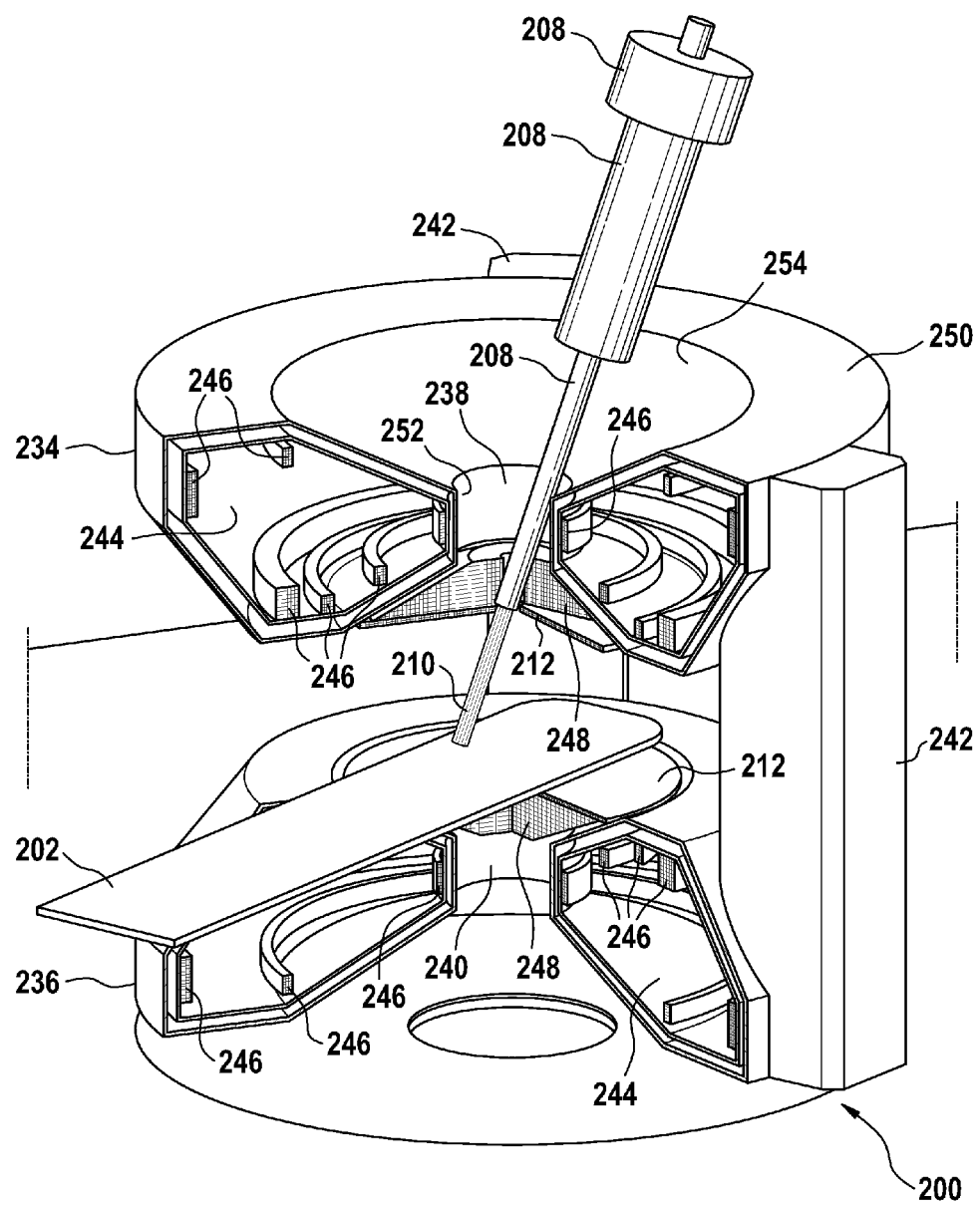
FIG. 2 shows a sectioned, perspective view of an embodiment of a therapeutic apparatus according to an embodiment of the invention.

FIG. 2 shows a sectioned, perspective view of an embodiment of a therapeutic apparatus according to an embodiment of the invention. The therapeutic apparatus comprises a magnetic resonance imaging system 200. The magnetic resonance imaging system comprises a first sub-magnet 234 and a second sub-magnet 236. The sub-magnets 234, 236 have a cryogenic chamber 244 and superconducting coils 246. The superconducting coils 246 are used to generate the magnetic field. The first sub-magnet 234 has a first central region 238 and the second sub-magnet 236 has a second central region 240. The magnetic field lines pass through these two central regions 238, 240. There are two cold supports 242 between the two sub-magnets 234, 236. The cold supports 242 are adapted for providing a rigid mechanical and a superconducting, electrical connection between the two sub magnets 234,236. There is a subject support 202 which is adapted for translational and rotational motion and is adapted for moving the subject so that the particle beam 210 is able to reach any portion of the subject. By having a combination of translational and rotational motion, the particle beam has multiple trajectories which can reach the same target zone. This is advantageous, because it allows the dose of radiation to the subject outside of the target zone to be spread over a larger portion of the subject. This reduces the chance of damage to the subject.

For acquiring magnetic resonance imaging data the magnetic resonance imaging system 200 also has radio frequency coils 212 and magnetic field gradient coils 248. The radio frequency coils 212 and the gradient coil 248 adjacent to the first sub-magnet 234 are adapted such that the particle beam is able to pass through them without striking them. In this embodiment the guiding means projects through the gradient coil 248 and the RF coil 212. The guiding means is adapted for adjusting the trajectory of the particle beam 210. The first sub-magnet 234 has a first central surface 242 and an external surface facing away from the means for generating a magnetic field 250. There is a beveled surface 254 between the external surface facing away from the means for generating a magnetic field 250 and the first central surface 252. This beveled surface 254 allows the guiding means 208 to be at a larger angle with respect to the magnetic field lines in the imaging zone.

The embodiment shown in FIG. 2 can be built by combining a high-field open MRI system, similar to the Philips Panorama high field open MRI system, and a guiding means 208 of a charged particle beam therapy system. The magnet can be an iron-free axi-symmetric superconducting coil system with active shielding; the strength of the main magnetic field can be approximately 1 Tesla, allowing high-quality fast imaging. The central hole in the magnet's cryostat 238 allows a charged particle guiding means 208 to protrude into the subject space of the scanner. In order to let the beam-tube 208 pass through, both the gradient coil 248 and the RF coil 212 can be adapted to have a hole in the central region. If the charged particle guiding means is oriented at an angle relative to the vertical axis of the magnet, the irradiation can be performed using more than one field by rotating the subject table about the vertical axis. Having the charged particle beam line in a fixed position relative to the magnet greatly simplifies the construction of the system in comparison to a rotating charged particle gantry. Having the charged particle beam system and the MRI magnet fixed relative to each other has the advantage that it simplifies the control of the charged particle beam trajectories and improves the robustness of the treatment system.

The charged particle beam scanning magnets are preferably located some distance away from the magnet, in order to minimize magnetic interference between the MRI system and the charged particle beam scanning system. The spread in beam trajectories between 30 MeV and 300 MeV protons is small enough that the differences can be compensated for by the beam scanning magnets. Hence neither the proton beam line nor the subject support 202 need to be mechanically moved to irradiate a line of voxels lying at various depths in the subject along a straight line coinciding with the un-distorted beam trajectory.

The top and bottom halves can be interconnected by means of at least one rigid cold support 242. A single support allows the subject support 202 to rotate to almost any orientation. In case two cold supports 242 are used, their angular positions relative to the proton guiding means 208 can be chosen such as to maximize the number of subject support positions not interfering with the cold supports 242.

The top plate 250 of the first sub magnet 234 preferably has a depression 254, which can be of conical shape, minimizing the length of the central hole 238 in the first sub magnet 234 through which the guiding means 208 enters the MRI system 200. This beveled surface 254 can also be used to locate auxiliary equipment belonging either to the MRI system 200 or to the charged particle guiding means 208. In order to reduce the stray field of the MRI magnets 234, 236 in the region above the magnet, the simple active shielding arrangement of the standard Panorama magnet (consisting of two large-diameter coils) can be refined by incorporating additional smaller shielding coils at a smaller diameter.

The relative position of the charged particle beam 210 and the superconducting magnet coils 246 is preferably selected such that no superconducting windings are directly exposed to the high-energy charged particles. This minimizes the risk that the sub magnets 234, 236 can be quenched by charged particle irradiation. In order to avoid radioactive activation of the system, the amount of construction material at the proximal side of the charged particle beam should be minimized as much as possible.

The irradiation of a lesion involves modulation of the charged particle energy, which controls the depth of the irradiation zone, small lateral displacement of the charged particle beam for short-range lateral distribution of the charged particles, translation of the subject support 202 in two directions in the horizontal plane for larger-scale lateral distribution of the charged particle energy and rotation of the subject support 202 (in conjunction with lateral displacements and energy adjustments) to reduce the energy deposition healthy tissue between the surface of the subject and the lesion to be treated (multiple-field treatment).

Embodiments of the invention may have one or more of the follow features:

the prediction of the exact beam trajectories, depending on charged particle energy and subject position, taking the magnetic field of the scanner into account, real-time update of beam steering parameters based on fast MRI images of the subject while the therapy is being applied. Preferably, these beam corrections are performed by means of the beam scanning magnets and the charged particle energy modulation, visualization of the charged particle beam by making use of the effect of the magnetic field generated by the charged particle beam on the phase of NMR-excited proton spins.

The charged particle beam and be generated by a cyclotron or synchrotron, similar to those being used in existing proton therapy systems, or by other types of charged particle accelerators (e.g. linac, high-energy pulsed laser, linear accelerator). The beam generated by the accelerator is delivered to the therapy station by means of a beam line system incorporating beam focusing and bending magnets and optionally beam switches distributing the beam over multiple treatment stations, which may or may not be equipped with MRI scanners. The accelerator may be capable of rapidly modulating the energy of the charged particles, as part of the compensation for the effects of organ motion. If the energy of the charged particles coming from the accelerator cannot be rapidly adjusted the treatment system can incorporate a fast modulator in the nozzle guiding the protons to the subject. Such a modulator may consist of a wedge-shaped slab of attenuating material, the position of which is controlled by a fast mechanical actuator. The thickness of the part of the slab in the path of the charged particle beam then determines the reduction of charged particle energy between the accelerator and the subject-side exit from the guiding means 208.

Figure 3:
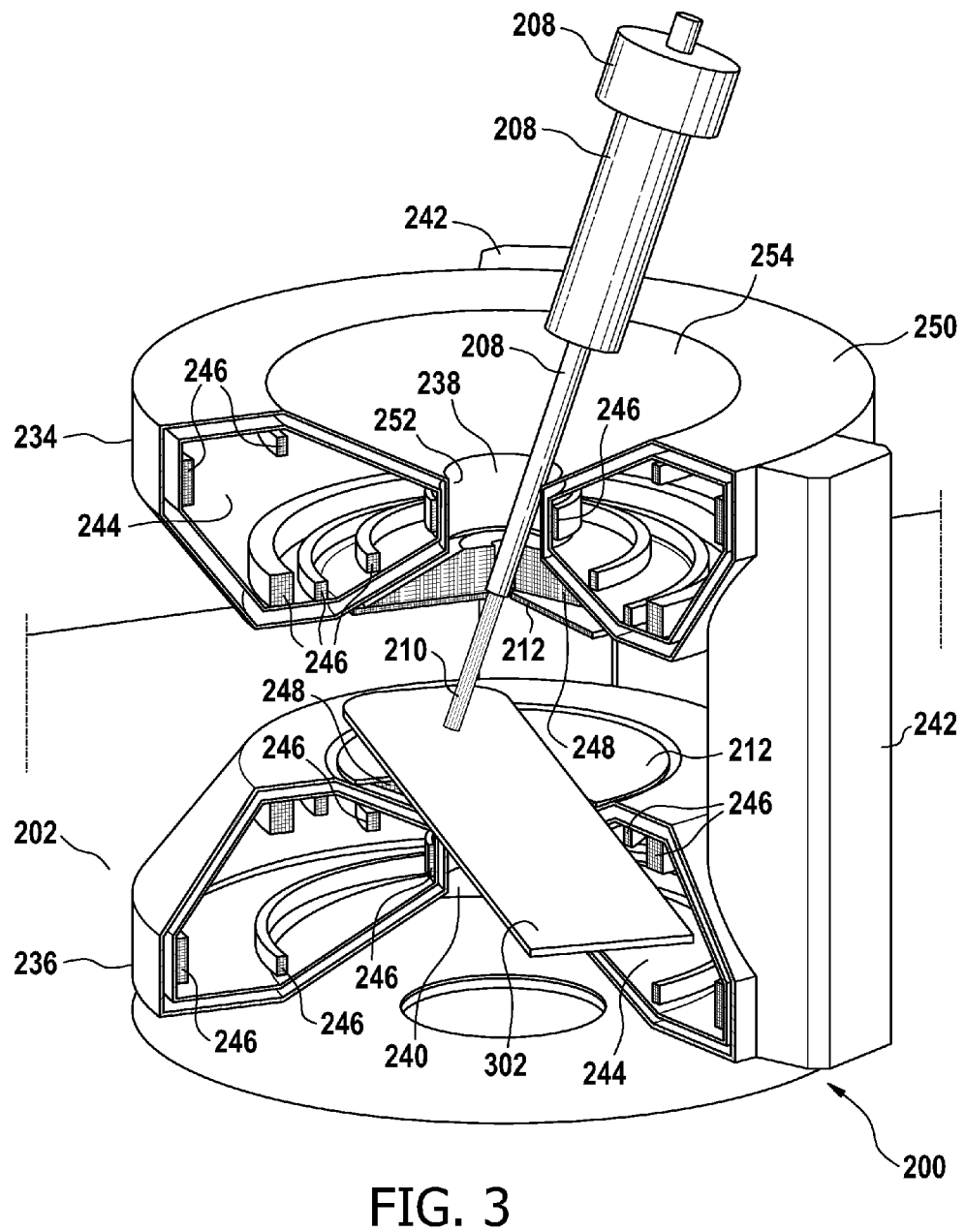
FIG. 3 shows a sectioned, perspective view of an embodiment of a therapeutic apparatus according to an embodiment of the invention.

FIG. 3 shows a section perspective view of an embodiment of a therapeutic apparatus according to an embodiment of the invention. This embodiment of the invention is identical to that shown in FIG. 2. As a result identical numerals are used to identify objects in this figure. The only difference between this figure and FIG. 2 is that the position of the subject support 302 is moved relative to the position of the subject support 202 in FIG. 2. This figure demonstrates how the subject support could be moved so different regions of a subject can be treated with a charged particle beam.

Figure 4:
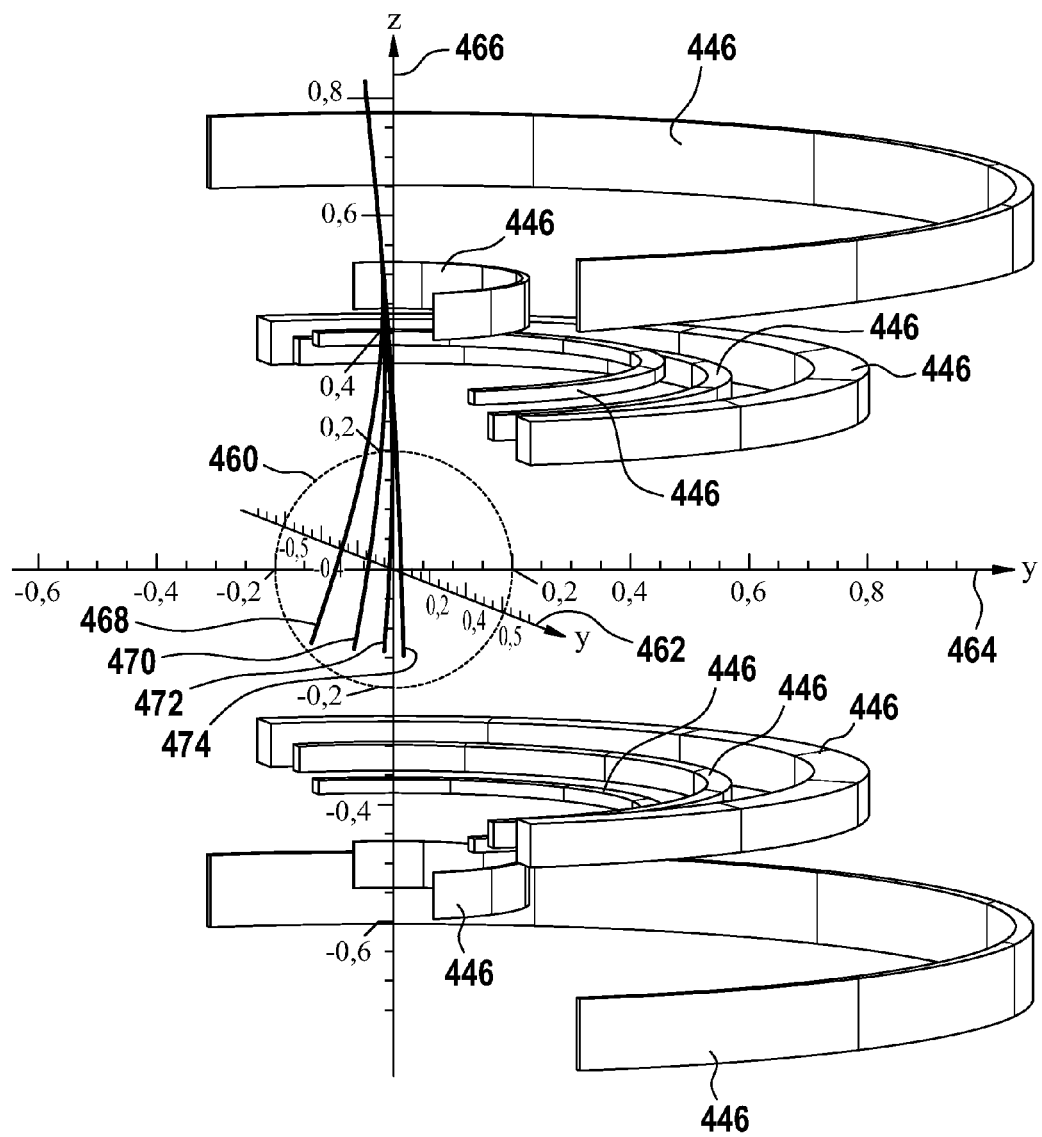
FIG. 4 shows calculated proton beam trajectories in the field of a 1.0 Tesla magnetic resonance imaging system.

FIG. 4 shows calculated proton beam trajectories in the field of a 1 Tesla magnetic resonance imaging system. This figure shows the arrangement of the superconducting coils 446 of the magnetic resonance imaging system. The arrangement of the superconducting coils in this figure is analogous to the arrangement of the superconducting coils shown in the embodiments of FIGS. 2 and 3. A region of uniform magnetic field 460 is shown in this diagram. Within this region, it would be possible to acquire magnetic resonance imaging data. The displacement from the axis of symmetry of the magnet and the center of the magnet is shown in the displacement along the x-axis 462, displacement along the y-axis 464, and displacement along the z-axis 466. The trajectory of a 10 MeV proton beam 468, a 30 MeV proton beam 470, a 100 MeV proton beam 472, and a 300 MeV proton beam 474 are shown.

LIST OF REFERENCE NUMERALS

100 Magnetic resonance imaging system
104 Magnetic field lines
106 Imaging zone
108 Guiding means
110 Beam of charged particles
112 Transceiver coil
114 RF transceiver
116 Subject
118 Angle between magnetic field lines and particle beam
120 Target zone
122 Computer
124 Hardware interface
126 Microprocessor
128 Computer program product
130 Zone determination means
132 User interface
134 First sub magnet
136 Second sub magnet
138 First central region
140 Second central region
148 Gradient coil
156 Gradient amplifier
158 Opening
200 Magnetic resonance imaging system
202 Subject support
208 Guiding means
210 Beam of charged particles
212 RF transceiver coil
234 First sub magnet
236 Second sub magnet
238 First central region
240 Second central region
242 Cold support
244 Cryogenic chamber
246 Superconducting coil 248 Gradient coil
250 External surface facing away from the means for generating a magnetic field
252 First central surface
254 Beveled surface
302 Subject support
446 Superconducting coil
460 Region of uniform magnetic field
462 Displacement along x axis
464 Displacement along y axis
466 Displacement along z axis
468 10 MeV proton trajectory
470 30 MeV proton trajectory
472 100 MeV proton trajectory
474 300 MeV proton trajectory

The invention claimed is:

1. A therapeutic apparatus comprising:
a magnetic resonance imaging generator configured to:
acquire magnetic resonance images in an imaging zone, include first and second sub magnets located above and below the imaging zone, each sub magnet surrounding a respective central region, the imaging zone surrounding a portion of a subject that includes a target zone, and
generate a magnetic field having magnetic field lines passing through the central regions of the first and second sub magnets;
a beam guide configured to guide a beam of charged particles along a path to the target zone, in the imaging zone the path and magnetic field lines of the magnetic field form an angle greater than 0 degrees and less than 30 degrees;
a processor configured to:
determine a location of the target zone within the subject using the magnetic resonance images,
determine effects on the beam of charged particles caused by the magnetic field using magnetic field data descriptive of the magnetic field; and
calculate a trajectory of the path based at least upon the effects on the beam of charged particles caused by the magnetic field; and
a beam controller configured to control the beam guide using the calculated trajectory to guide the beam along the calculated trajectory;
wherein the first sub magnet has an external surface facing away from the magnetic field generator that intersects a first central surface that surrounds the central region of the first magnet, wherein there is a beveled surface between the external surface and the first central surface which allows the beam to pass.

2. A therapeutic apparatus comprising:
a magnetic resonance imaging generator having first and second sub magnets located above and below an imaging zone, each sub magnet surrounding a respective central region, for acquiring a set of magnetic resonance imaging data in the imaging zone, and for generating a magnetic field having magnetic field lines passing through the central regions of the first and second sub magnets;
a beam guide for guiding a beam of charged particles along a path to a target zone within a subject, in the imaging zone the path and the magnetic field lines of the magnetic field form an angle greater than 0 degrees and less than 30 degrees;
a processor configured to:
determine a location of the target zone within the subject using the set of magnetic resonance imaging data, and
calculate a trajectory of the path of the beam using magnetic field data descriptive of the magnetic field; and
a beam controller configured to control the beam guide using the calculated trajectory such that the beam follows the calculated trajectory;
wherein the first sub magnet has an external surface facing away from the magnetic field generator that intersects a first central surface that surrounds the central region of the first magnet, wherein there is a beveled surface between the external surface and the first central surface which allows the beam to pass.

3. The therapeutic apparatus of claim 1, wherein the processor is further configured to:
calculate an energy loss of the beam within the subject, and
adjust the calculated trajectory using the energy loss.

4. The therapeutic apparatus of claim 1, wherein in the imaging zone, the path and the magnetic field lines of the magnetic field form an angle selected from ranges of between 5 degrees and 25 degrees, the calculated trajectory of the beam comprises more than one calculated trajectory, and the beam controller is configured to switch between the more than one calculated trajectory during therapy to minimize the exposure of portions of the subject outside of the target zone to the beam.

5. The therapeutic apparatus of claim 1, wherein:
the magnetic resonance imaging generator is further configured to acquire magnetic resonance images at periodic intervals;
the processor is further configured to:
monitor motion of the target zone using the magnetic resonance images acquired at periodic intervals,
monitor internal motion of the subject along the beam trajectory using the magnetic resonance images acquired at periodic intervals, and
adjust the calculation of the calculated trajectory to compensate for motion of the target zone, and
the beam controller is configured to adjust the beam trajectory using adjustments to the calculated trajectory.

6. The therapeutic apparatus of claim 1, wherein the beam guide comprises:
charged particle optics for adjusting the beam trajectory, and
an adjustable attenuator for modulating the energy of charged particles comprising the beam.

7. The therapeutic apparatus of claim 1, wherein the magnetic resonance imaging system is further configured to measure the trajectory of charged particles within the imaging zone, wherein the beam controller is configured to adjust the beam trajectory using the measured trajectory.

* * * * *